United States Patent [19]

Bachorik

[11] 4,399,815
[45] Aug. 23, 1983

[54] PNEUMATIC THERAPEUTIC HEEL AND ANKLE GUARD

[76] Inventor: Joan E. Bachorik, R.D. 1, Oneonta, N.Y. 13820

[21] Appl. No.: 263,304

[22] Filed: May 13, 1981

[51] Int. Cl.³ .............................................. A61F 5/30
[52] U.S. Cl. .................................... 128/153; 128/85
[58] Field of Search ................... 128/25 B, 26, 77, 80, 128/84 A, 85, 87 R, 89 R, 153, 165, 166, DIG. 20; 441/40, 129, 132; 114/345

[56] References Cited

U.S. PATENT DOCUMENTS

| 1,784,032 | 12/1930 | Stern | 128/153 |
| 2,531,074 | 11/1950 | Miller | 128/87 R |
| 2,655,916 | 10/1953 | Timmins | 128/87 R |
| 4,263,905 | 4/1981 | Couch | 128/153 |
| 4,266,298 | 5/1981 | Graziano | 128/89 R |

FOREIGN PATENT DOCUMENTS 2251643  6/1973  Fed. Rep. of Germany .... 128/89 R

Primary Examiner—Kyle L. Howell
Assistant Examiner—Max F. Hindenburg

[57] ABSTRACT

A pneumatic therapeutic heel and ankle guard is provided. The heel and ankle guard is comprised of an elongated inflatable base member. An inflatable elongated "U"-shaped tube comprised of two elongated leg members and a "U"-shaped member connects one end of each member. The leg members are mounted in spaced apart relationship to the top surface of the base member. The "U"-shaped member extends beyond the front of the base member. A patient's leg is rested on the base member surrounded by the "U"-shaped tube. The sole of the foot may rest upon the "U"-shaped member connecting each of the leg members. The leg protector prevents heel and ankle contact pressure allowing for the quick healing of heel sores, known more specifically as decubitus ulcers.

7 Claims, 4 Drawing Figures

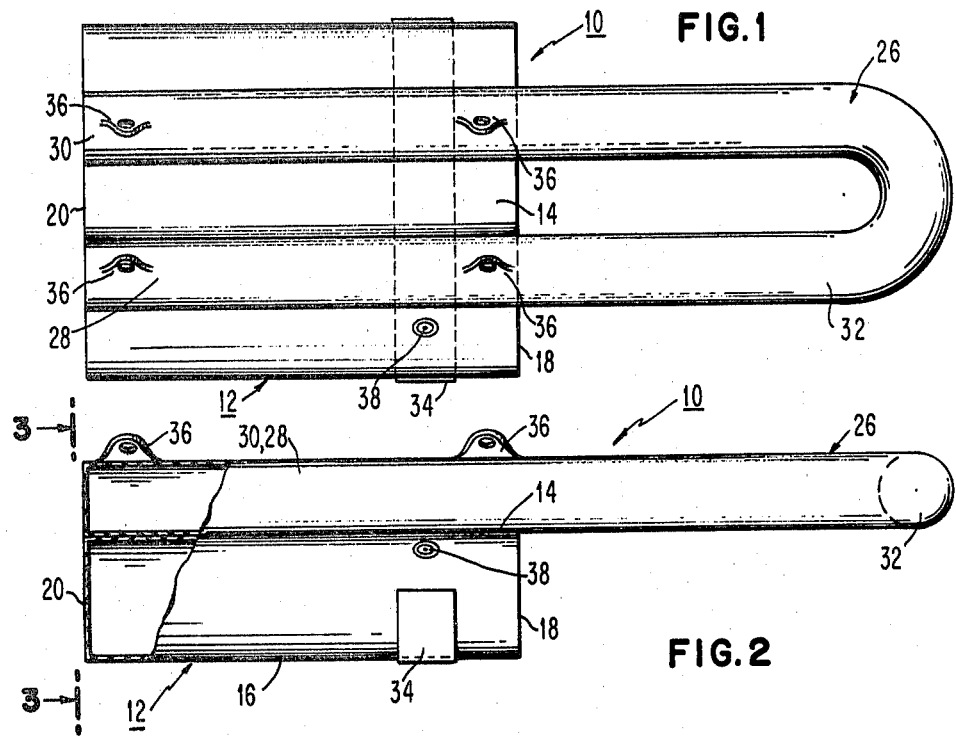
FIG. 1
FIG. 2
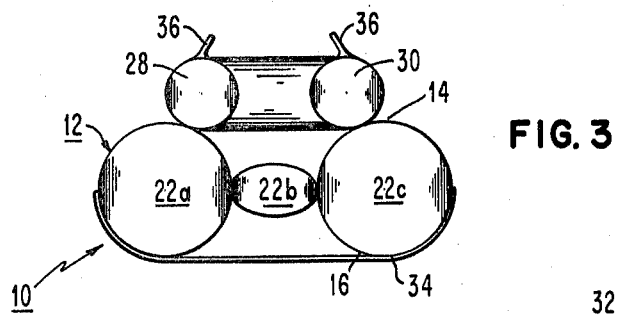
FIG. 3
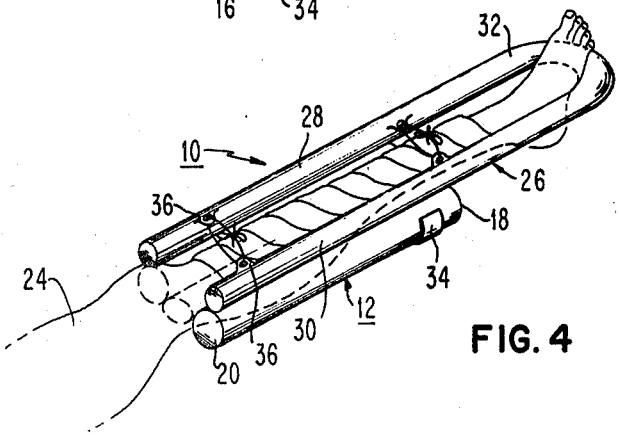
FIG. 4

PNEUMATIC THERAPEUTIC HEEL AND ANKLE GUARD

BACKGROUND OF THE INVENTION

1. Field of the Invention

This invention relates to a heel and ankle protective device, and more particularly to a heel and ankle protector which prevents or allows for the quick healing of heel sores.

2. Prior Art

Many patients have suffered from ulcers or bed sores, particularly around the ankles and heel, caused by these portions of the body coming into abrasive contact with the sheets of the bed and/or due to reduced blood circulation caused by pressure on the ankle and heel from the weight of the foot resting on the bed. These ulcers or bed sores are known more specifically as decubitus sores. Some of the prior art devices used for the prevention of such sores are exemplified by the following U.S. Patents:

U.S. Pat. No. 2,983,272 to Hunstiger;
U.S. Pat. No. 3,011,494 to McGowan;
U.S. Pat. No. 3,407,811 to Stubbs;
U.S. Pat. No. 3,508,544 to Moore et al;
U.S. Pat. No. 3,511,233 to Holy, Jr.;
U.S. Pat. No. 3,670,725 to Gaylord, Jr.;
U.S. Pat. No. 3,721,237 to Alessio;
U.S. Pat. No. 4,076,022 to Walker; and
U.S. Pat. No. 4,150,442 to Boone.

All of the aforementioned U.S. patents generally wrap the ankle or foot completely or partially to prevent the ankle or foot from coming in contact with the bed or sheet. Such devices are generally fairly ineffective in being occlusive so that the patients skin begins to sweat and chafe and becomes inflamed and irritated. Additionally, all of these aforementioned devices generally consist of a fabric which is wrapped around the foot, ankle or leg; which makes them bulky and cumbersome and generally difficult to sanitize in that they must either be disposable or washable, the washing taking the conventional time for washing and drying.

Additionally, there are various inflatable devices which generally are used to immobilize the leg when it is fractured, i.e. inflatable splints. These types of devices are exemplified by the following U.S. patents:

U.S. Pat. No. Re. 27,957 to Larson;
U.S. Pat. No. 2,651,302 to Berry;
U.S. Pat. No. 3,164,152 to Nicoli;
U.S. Pat. No. 3,338,237 to Sconce;
U.S. Pat. No.3,351,055 to Gottfried; and
U.S. Pat. No. 4,157,713 to Clarey.

None of these aforementioned inflatable devices are designed to prevent sores or ulcers of the foot, heel and ankle. All of these aforementioned inflatable splint devices, generally, completely surround the leg and ankle and are not designed for the purpose of preventing bed sores and ulcers of the foot, heel and ankle.

OBJECTS AND SUMMARY OF THE INVENTION

It is a principle object of this invention to provide a pneumatic therapeutic heel and ankle guard to prevent heel and ankle ulcers in bedridden patients.

It is another object of this invention to provide a foot and leg support which keeps the heel and ankle portions of the foot out of contact with the bedding.

It is another object of this invention to provide a heel and ankle guard which is flexible and light so that it will not be annoying or burdensome to the patient wearing the device.

It is a further object of this invention to provide a heel and ankle guard which is relatively inexpensive which is light in weight, comparatively cool, and non-allergenic.

It is a further object of this invention to provide a foot and leg support for use in the prevention of ulcers of the heel and ankle which is inflatable and can be easily inflated, deflated and stored.

It is a further object of this invention to provide a heel and ankle guard which provides for improved circulation of air about the heel of the foot.

The foregoing objects as well as other objects of this invention are achieved by a pneumatic therapeutic heel and ankle guard comprising:

(a) an elongated inflatable base member having a top and bottom surface and front and rear ends;
(b) an inflatable elongated "U"-shaped tube comprised of two elongated leg members and a "U"-shaped member connecting one end of each leg member, wherein the leg members are mounted in spaced apart relationship to the top surface of the base member and the "U"-shaped member extends beyond the base member.

BRIEF DESCRIPTION OF THE DRAWINGS

FIG. 1 is a plan view of an embodiment of the heel and ankle guard of this invention;

FIG. 2 is a partial sectional view of the embodiment of the heel and ankle guard depicted in FIG. 1;

FIG. 3 is a sectional view taken along line 3—3 of FIG. 2; and

FIG. 4 is a perspective view of an embodiment of the heel and ankle guard depicted in FIGS. 1 through 3 strapped to the leg of a patient.

DETAILED DESCRIPTION OF THE INVENTION

Referring to FIGS. 1-4, the pneumatic therapeutic heel and ankle guard is generally designated (10). The guard (10) is comprised of an elongated inflatable base member, generally designated (12). The base member (12) has a top surface (14), a bottom surface (16) and front and rear ends (18 & 20), respectively). Preferrably, the base member (12) is comprised of a plurality of elongated inflatable tubes (22). These tubes (22) are longitudinally joined to each other. In the preferred embodiment depicted in FIGS. 1-4, the base member (12) is comprised of two side tubes (22a & 22c) jointed to a central tube (22b).

As shown more clearly in FIG. 3, the two side tubes (22a & 22c) are preferrably of a larger diameter than the central tube (22b). For example, for a base member (12) to fit a normal sized person, it would be desirable to have the two side tubes (22a & 22c) of $4\frac{1}{2}$ inches in diameter and the central tube (22b) of about 3 inches in diameter. This would provide a base member (12) of about 10 inches in width. The top surface of the central tube (22b) would thus be about $\frac{3}{4}$ of an inch below the top surface of the side tubes (22a & 22c). The leg (24) could then rest on top of the central tube (22b) and be somewhat surrounded by the side tubes (22a & 22c) so that the leg does not slide off the base member (12).

An inflatable elongated "U"-shaped tube, generally designated (26) is mounted to the top surface (14) of the base member (12). This "U"-shaped tube is comprised of two elongated leg members (28 & 30) and a "U"-shaped member (32) connecting one end of each elongated leg member (28 & 30). The elongated leg members (28 & 30) are mounted in spaced apart relationship to the top surface (14) of the base member (12). The "U"-shaped member (32) extends beyond the front end (18) of the base member (12).

In the preferred embodiment depicted in FIGS. 1-4 the elongated leg members (28 & 30) are each mounted to a side tube (22a & 22c). This is shown more clearly in FIG. 3. Thus the two elongated leg members (28 & 30) further surround the patients leg (24) so that it is resting securely on the base member (12). The patient's leg when resting upon the base member (12), surrounded by "U"-shaped tube (26), has the sole of the foot resting upon "U"-shaped member (32). The diameter of the side tubes (22a & 22c) is such that the heel is elevated above the bed sheet. Additionally, the distance that the "U"-shaped member extends beyond the front end (18) of the base member (12) is such so as to provide free air circulation around the ankle. Preferably the distance between the front end (18) of base member (12) and the end of the "U"-shaped member (32) is about 6 inches. Further, the angle between the base member (12) and leg members (28 & 30) allows for air circulation along the length of the patient's leg. Preferably the diameter of each is about 2½ inches. The preferred overall length of the heel and ankle guard is about 18 inches.

In the preferred embodiment depicted in FIGS. 1-4 an elongated restraining band (34) is connected at each of its ends to a side tube (22a & 22c). This restraining band (34) is designed to prevent the lateral expansion of the base member (12) as the patient's leg (24) is rested upon the base member (12). Preferably the restraining band (34) is adjacent to the bottom surface (16) of the base member (12) at the front end. Such positioning of the restraining band (34) prevents contact of the restraining band (34) with the bottom of the patient's leg (24).

The heel and ankle guard, as shown in FIGS. 1-4, preferably has a plurality of tie means (36), e.g. eyes, used for securing the length of the elongated leg members (28 & 30) along the top surface of the patient's leg. Such tie means secure the heel and ankle guard (10) to the patient's leg (24).

The heel and ankle guard has a means for inflation, generally designated (38) (FIGS. 1 and 2) which can also be used for inflating the foot and leg guard. Prior to use it is inflated and after use it is deflated and stored away.

In use, the patient's leg (24), is preferably covered with a cotton sleeve, similar to the conventional orthopedic stocking, to minimize friction between the leg (24) and the base member of the guard or support (10). The patient's leg (24) is then placed upon the base member (12). In the preferred embodiment the patient's leg (24) rests upon the top surface of central tube (22b) surrounded by side tubes (22a & 22c) and elongated leg members (28 & 30). The sole of the foot may rest upon the "U"-shaped member (32). The heel is elevated above the sheet of the bed.

Heel and ankle guard (10) of this invention is made by the conventional means for making such devices. Such means are incorporated in all of the aforementioned U.S. patents relating to inflatable splints. the entire disclosures of all of these aforementioned references are incorporated herein by reference.

Preferably the walls of the inflatable foot and leg guard are made from an FDA approved material which is flexible and capable of retaining air pressure in the chamber between the walls without stretching or ballooning. Such material is typically an 8 to 12 gauge poly-vinyl chloride, preferably an 8 gauge poly-vinyl chloride.

In conclusion, it may be seen that the present invention provides a novel heel and ankle guard which has significant advantages over the devices of the prior art. Variations may be made in the form of the invention shown without departing from its scope which is to be limited only by the appended claims.

What is claimed is:

1. A pneumatic therapeutic heel and ankle guard for bed ridden patients comprising:
    (a) an elongated inflatable base member having a top and bottom surface and front and rear ends;
    (b) an inflatable elongated "U"-shaped tube comprised of two elongated leg members and a "U"-shaped member connecting one end of each leg;
wherein each leg member is mounted along the length of the top surface of the base member with sufficient space between the leg members to surround the patients leg so that the leg rests securely on the top surface of base member and between the leg members, and
    wherein the "U"-shaped member extends beyond the front of the base member a sufficient distance to provide free air circulation around the ankle while the sole of the patients foot rests upon "U"-shaped member and permits the free range of motion of the foot.

2. The heel and ankle guard of claim 1, wherein the base member is comprised of a plurality of elongated inflatable tubes joined longitudinally side-by-side to each other.

3. The heel and ankle guard of claim 2, wherein the base member is comprised of two side tubes joined to a central tube.

4. The heel and ankle guard of claim 3, wherein each of the elongated leg members is mounted to an opposed side tube.

5. The ankle guard of claim 1, wherein an elongated restraining band is connected at each of its ends to an opposed side tube for restraining lateral expansion of the base member.

6. The heel and ankle guard of claim 5, wherein the restraining band is juxtaposed against the bottom surface of the base member at the front end.

7. The heel and ankle guard of claim 1, wherein a plurality of tie means connect the tops of leg members along their lengths for securing the heel and ankle guard to the leg of the patient.

* * * * *